United States Patent [19]

Grollier et al.

[11] Patent Number: 4,460,488

[45] Date of Patent: Jul. 17, 1984

[54] PLANT EXTRACTION RESIDUE AS A THICKENING OR OPACIFYING AGENT FOR A COSMETIC COMPOSITION

[75] Inventors: Jean-François Grollier, Paris; Josiane Allec, Pierrefitte; Chantal Fourcadier, Paris; Georges Rosenbaum, Asnieres; Patrick Darmenton, Villejuif, all of France

[73] Assignee: Societe Anonyme dite: L'OREAL, Paris, France

[21] Appl. No.: 411,539

[22] Filed: Aug. 25, 1982

Related U.S. Application Data

[62] Division of Ser. No. 221,636, Dec. 31, 1980, Pat. No. 4,358,286.

[30] Foreign Application Priority Data

Jan. 4, 1980 [FR] France .................................. 80 00093

[51] Int. Cl.$^3$ ................................................. C11D 7/44
[52] U.S. Cl. ..................................... 252/89.1; 252/90; 252/132; 252/174.17; 252/315.3; 252/550; 252/551; 252/542; 252/DIG. 13; 424/195; 424/70

[58] Field of Search .................. 252/89.1, 90, 550, 551, 252/DIG. 13, 315.3, 174.17; 424/74, 195, 364; 260/236.5

[56] References Cited

U.S. PATENT DOCUMENTS

| 2,353,686 | 7/1944 | Brown | 252/368 |
| 3,115,410 | 12/1963 | Huffman | 252/315.3 |
| 3,170,916 | 2/1965 | Dziengel | 260/236.5 |
| 3,929,997 | 12/1975 | Matsui | 424/95 |
| 4,148,762 | 4/1979 | Koch et al. | 252/544 |

FOREIGN PATENT DOCUMENTS 833984 5/1981 U.S.S.R. .

Primary Examiner—P. E. Willis, Jr.
Attorney, Agent, or Firm—Cushman, Darby & Cushman

[57] ABSTRACT

A cosmetic composition for application to human hair or skin contains as a thickening or opacifying agent therefore, the residue of a plant extracted to remove all of at least one of its dye, essential oil, olfactory or therapeutic or cosmetic active principles. The residue is in powder form having a granulometry less than 125 microns and is present in said composition in an amount ranging from 2 to 95 percent by weight based on the total weight of said composition.

13 Claims, No Drawings

PLANT EXTRACTION RESIDUE AS A THICKENING OR OPACIFYING AGENT FOR A COSMETIC COMPOSITION

This is a division of application Ser. No. 221,636 filed Dec. 31, 1980, now U.S. Pat. No. 4,358,286.

This invention has for its object new cosmetic compositions for treating hair and skin containing a powder of plant origin obtained from extraction residues of various plants.

The pharmaceutical industry, like the cosmetics industry, uses extracts of various plant substances as active substances in numerous formulations.

These extracts are obtained by different known processes and particularly by maceration, digestion, decoction, infusion or leaching and leave as residues large amounts of plant materials that so far have found no particular use.

Actually, it would be considered that these materials are essentially deprived of their active principles and would not have any application and have generally been destroyed.

It has now been found after varied research that these plant materials can indeed be used successfully in the fields of cosmetics.

The invention thereof rests on the discovery that certain plants having very specific properties due to their active principles can, after extraction, exhibit totally new properties.

Consequently, according to the invention, it is possible to use not only extraction residues of plants having active cosmetic principles but also extraction residues of plants having therapeutic or possibly toxic, irritating or sensitizing active principles.

Actually, after pulverizing, the extraction residues give powders of determined granulometry, which can be incorporated as charges in various formulations and, depending on the origin of the powder, lead to obtain different supports having particularly desirable cosmetic properties.

In a general way, these powders can intervene as thickening or opacifying agents and give the compositions an excellent lubricating quality making their application easy.

Moreover, it has been noted that the compositions containing these powders are particularly gentle to apply and further make a very good elimination possible.

Regardless of their origin, these powders can advantageously replace the various charges usually used in cosmetic compositions such as talc, titanium oxide, etc.

Finally, it has been found that some of these powders make it possible to treat effectively greasy skin and hair exhibiting a greasy appearance by absorption of sebum.

This invention has for its object by way of new industrial products a cosmetic composition containing a very fine powder of plant origin obtained from plant extraction residues, said powder having a granulometry less than 125 microns and preferably less than 80 microns.

This powder of plant origin is used according to the invention as a support, opaquing agent or even active agent in the case of absorption of the sebum of greasy hair.

According to the invention, there can be used as powders those obtained by pulverizing or micronizing of:

plant residues after extraction of dye principles,
plant residues after extraction of essential oils,
plant residues after extraction of therapeutic and/or cosmetic active principles,
plant residues after extraction of olfactory active principles.

As plant residues after extraction of dye principles, there can be cited:

Roucou, tumeric, paprika, tomato, red beet, hibiscus, grape, spinach, nettle, alfalfa and bloodroot.

As plant residues after extraction of essential oils there can be cited:

basil, bitter orange, bergamot, cinnamon, caraway, cassia, lemon, cypress, fennel, juniper, gentian, geranium, ginger, clove, lavender, marjoram, milfoil, myrtle, niaouli, origanum, pine, rosemary, rose, sandalwood, savory, sassafras, sage, marigold, thyme, lime, vervain, violet, ylang-ylang, cajeput, orange and mint.

As plant residues after extraction of the therapeutic and/or cosmetic active principles there can be cited:

hawthorn, eucaluptus, gentian, chinchona, saponaria, (leaves or roots), arnica (leaves or roots), inula, bistort, Roman camomille, cascara, knapweed, hops, horse chestnut, lignum vitae, witch hazel (leaves), rhubarb, passion flower, quebracho, ratany (roots), sarsaparilla, shepherd's knot, valerian (roots), henna, aloes, pineapple, black alder, burdock, elder, fenugreek, soap bark, oak, marsh mellow, ruscus, ivy, feverfew, mallow, melilot, St. John's wort, and horsetail.

As plant residues after extraction of olfactory active principles there can be cited:

plum tree evernia, cistus and iris.

According to the invention there are preferably used the extraction residues of hawthorn, eucaluptus, saponaria, arnica, horse chestnut, sarsaparilla, cistus, nettle, oak, ruscus, ivy, rose, horsetail, milfoil, witch hazel or lavender.

These residues result from the various extraction processes generally used to obtain active principles and particularly by maceration, digestion, decoction, infusion or leaching.

Preferably according to the invention extraction residues obtained by leaching are used.

The solvents used in these processes can be water or an organic solvent selected from:

(1) monoalcohols such as:
alkanols having between 1 and 8 carbon atoms as ethanol, isopropanol, tertiobutyl alcohol, butyl alcohols or cyclohexanol.

(2) polyalcohols such as:
alkylene glycols such as ethyleneglycol or propyleneglycol.

(3) glycol ethers such as:
mono, di and triethyleneglycol-monoalkylether such as, for example, ethyleneglycol-monoethylether or diethyleneglycol-monoethylether.

(4) esters as methyl, ethyl or butyl acetate, ethyleneglycol monomethylether acetate, ethyleneglycol monoethylether acetate or ethyl acetylacetate.

(5) hydrocarbons such as:
butane, isobutane, propane, hexane or benzene.

(6) ketones such as:
acetone, methylethylketone, or methylisobutylketone.

(7) ethers such as:
diethylether, isobutylmethylether or diisopropylether, and (8) other solvents such as: diethyl carbonate, dimethyl carbonate, dimethylformamide, dioxane, tetrahydrofuran, dimethylsulfoxide, or carbon tetrachloride, these solvents being able to be used alone or in mixture. The preferred solvents are anhydrous solvents or their mixtures having a boiling point below or equal to 100° C.

In particular it is possible according to the invention to use residues left by the process described in French patent No. 1,520,375.

The extraction residues obtained by these processes are then finely ground or micronized in suitable apparatus to obtain powders with a granulometry less than 125μ and preferably less than 80μ.

The powder concentration in the compositions according to the invention varies as a function of their nature so that some can contain only a relatively slight percentage of powder whereas others, on the contrary, can be made up exclusively of them. This concentration therefore can vary between 2 and 95% and preferably between 3 and 50% in relation to the total weight of the composition.

The powders of plant origin obtained from extraction residues can go into making most cosmetic compositions.

Of these compositions there can particularly be cited creams, gels, makeups, skin masks, hair dyeing or bleaching products, permanents, uncurling products, hair rinse products to be applied before or after a hair treatment or blow-dry lotions.

Moreover, these powders can also go into making certain compositions, better known as "plasters," intended to be applied to hair possibly after being diluted with water. These "plasters" can contain, besides various standard ingredients, dyes and particularly nitro dyes of the benzene series, azoics, anthraquinones, indoamines, indoaniline, indophenols, etc. Further, the powders can be used as dry shampoos.

These powders of plant origin very particularly are used in shampoos because they make it possible to improve their consistency and facilitate their application.

The shampoos according to the invention, whose appearance depends on the powder concentration, contain an anionic, nonionic, cationic, amphoteric surfactant or a mixture of them as conventionally used in this type of formulation.

In certain cases the compositions according to the invention can be packaged in the form of an aerosol and in these cases powders with a relatively very fine granulometry, preferably less than 10μ, are used to avoid any risk of damaging the values. The propellant can be carbon dioxide, nitrogen, nitrous oxide, volatile hydrocarbons such as butane, isobutane, propane or preferably fluorocarbons and/or chlorocarbons.

It goes without saying that the compositions according to the invention can contain any other ingredient used in cosmetics such as perfumes, dyes, preservatives, antioxidizing agents, sequestering agents, thickeners, softeners, synergists, foam stabilizers, solar filters, peptizers, the nature of these ingredients depending on the application contemplated.

According to a particular embodiment the compositions contain at least a cationic polymer, these polymers preferably being of the polyamine, polyaminoamide or quaternary polyammonium type, the amine or ammonium group being a part of the polymer chain or being connected to it.

There will now be given by way of illustration and without any limiting character several examples of cosmetic compositions for the skin and hair containing a powder of plant origin obtained from plant extraction residues.

EXAMPLES OF COMPOSITIONS

Example A

A cream shampoo is prepared according to the invention by mixing the following ingredients:

| | |
|---|---|
| powder of residues of extraction with ethanol of micronized soponaria a granulometry less than 10μ | 16 g |
| palmetto oil sarcosinate neutralized to 40% of active material sold under the name "Medialan KF" by the Hoechst company | 15 g |
| cycloimidazoline derivative of coconut oil at 38% active material sold under the name "Miranol C 2M" by the Miranol company | 18 g |
| sodium lauryl ether sulfate at 30% of active material | 28 g |
| polymer of hydroxyethylcellulose and epichlorohydrin quaternized with trimethylamine with a viscosity of 400 CPO sold under the name "JR 400" by the Union Carbide company | 0.1 g |
| 5-bromo-5-nitro-1,3-dioxane | 0.3 g |
| water sufficient for | 100 g |

This shampoo exhibits a good viscosity and is easy to apply to the hair.

After the hair is washed, it easily untangles; the dry hair is soft and bouffant.

In this example, the powder of residues from saponaria extraction can be replaced by a powder of the same granulometry with residues of ethanol extraction of ivy, of residues of acetone extraction of nettle or residues of isopropanol extraction of eucalyptus.

Example B

There is prepared according to the invention a cream shampoo packaged in aerosol form by mixing 45 g of composition A above with 5 g of a propellant mixture made up of Freon 114 and Freon 12 in a 43/57 ratio.

Example C

A plaster is prepared according to the invention by mixing the following ingredients:

| | |
|---|---|
| powder of residues of ethanol extraction of ground hawthorn having a granulometry less than 60μ | 12 g |
| montmorillonite sold under the name "Gelwhite USP" by the Euroclay company | 12 g |
| gum tragacanth | 1 g |

At the time of use this powder is diluted in 100 g of water then applied to washed and wiped hair.

After standing 10 minutes, it is rinsed abundantly with water and the hair is soft to touch.

In this example the powder of residues of hawthorn extraction can be replaced with a powder of the same granulometry of residues of ethylene glycol extraction of horsetail or residues of extraction with a butane-isobutane mixture (50-50) of lavender.

Example D

A dye plaster is prepared according to the invention by mixing the following ingredients:

| | |
|---|---|
| powder of residues of ethanol extraction of micronized | 30 g |

-continued

| | |
|---|---|
| saponaria having a granulometry less than 10µ | |
| rye flour | 1.5 g |
| wheat flour | 1.5 g |
| dyes | |
| 1-hydroxy 3-nitro 4-amino benzene | 0.25 g |
| 1-hydroxy 3-nitro 4 N (β-hydroxyethyl) amino benzene | 0.005 g |

This powder is diluted at the time of use in 100 g of water.

The resulting composition is then applied to washed and wiped hair then after standing 30 minutes is rinsed abundantly with water. Initially dark blond hair exhibits a beautiful intense reddish copper glint.

Example E

An "oil plaster" is prepared according to the invention by mixing the following ingredients:

| | |
|---|---|
| powder of residues of ethanol extraction of pulverized arnica having a granulometry less than 40µ | 30 g |
| avocado oil | 50 g |
| castor oil oxyethylenated with 33 moles of ethylene oxide | 20 g |

This composition is applied to dirty hair before a shampoo.

After standing 20 minutes, it is rinsed abundantly with water and a standard shampoo is performed.

After rinsing and drying the hair exhibits a soft appearance and is pleasant to touch.

Example F

A dry aerosol shampoo is prepared according to the invention by mixing the following ingredients:

| | |
|---|---|
| powder of residues of ethanol extraction of micronized hawthorn having a granulometry less than 10µ | 3 g |
| powder of residues of ethanol extraction of micronized saponaria having a granulometry less than 10µ | 3 g |
| methylene chloride | 10 g |
| perfume sufficient amount | |
| isobutane/butane at 4 kg/m² (75/25) sufficient for | 100 g |

In this example the powder of residues of extraction of saponaria can be replaced by a powder of the same granulometry of residues of extraction with a water+ethanol mixture of milfoil.

Example G

An antiperspiration powder is prepared by mixing the following ingredients:

| | |
|---|---|
| powder of residues of ethanol extraction of micronized hawthorn having a granulometry less than 10µ | 45 g |
| powder of residues of ethanol extraction of micronized saponaria having a granulometry less than 10µ | 42 g |
| aluminum hydrochloride | 10 g |
| magnesium carbonate | 3 g |

Example H

The following ingredients are mixed to prepare a face mask:

| | |
|---|---|
| Guar gum | 1.5 g |
| α-escin | 0.5 g |
| gelatin | 1.2 g |

-continued

| | |
|---|---|
| saponaria extract enriched with saponin | 2 g |
| titanium oxide | 7 g |
| starch | 8 g |
| clay | 5 g |
| powders of residues of ethanol extraction of micronized saponaria having a granulometry less than 30µ sufficient for | 100 g |

Before application to the face, the resulting composition is mixed in water until a pasty consistency is obtained.

In this example the powder of the saponaria extraction residues can be replaced by a powder of the same granulometry of residues of ethanol extraction of ruscus.

Example I

A mask in the form of cream is prepared according to the invention by mixing the following ingredients:

| | |
|---|---|
| Veegum HV (Mg and Al silicate) sold by the Vanderbilt company | 3 g |
| glycerin | 5 g |
| Aubigum X 2 (red algae extract) | 2.5 g |
| powder of residues of ethanol extraction of horse chestnut having a granulometry less than 20 µ | 10 g |
| titanium oxide | 2.8 g |
| preservative | 0.2 g |
| perfume | 0.1 g |
| sterile demineralized water sufficient for | 100 g |

In this example the powder of residues of horse chestnut extraction can be replaced advantageously with a powder of residues of hexane extraction of rose of the same granulometry.

Example J

A mask in cream form is prepared according to the invention by mixing the following ingredients:

| | |
|---|---|
| powder of residues of ethanol extraction of micronized hawthorn having a granulometry less than 10µ | 18 g |
| propylene glycol | 8 g |
| sodium lauryl sulfate | 1.2 g |
| camphor | 0.02 g |
| Carbopol 940 (carboxyvinyl polymer) | 0.3 g |
| propyl para-hydroxybenzoate | 0.1 g |
| methyl para-hydroxybenzoate | 0.2 g |
| perfume | 0.2 g |
| sterile demineralized water sufficient for | 100 g |

In this example the powder of the residues of hawthorn extraction can be replaced with a powder of the same granulometry of residues of extraction with a mixture of water+ethyleneglycol-monoethylether of witch hazel.

Example K

A dye plaster is prepared according to the invention by mixing the following ingredients:

| | |
|---|---|
| powder of residues of ethanol extraction of pulverized saponaria having a granulometry less than 90µ | 40 g |
| powder of residues of ethanol extraction of pulverized hawthorn having a granulometry less than 110 µ | 10 g |
| Juglone (5-hydroxy-1,4-naphthoquinone) | 2 g |
| red pectin 3 G sold by the Unipectine company | 3 g |
| pure anhydrous sodium carbonate | 5 g |
| trioxymethylene in powder | 0.3 g |

-continued

| | |
|---|---|
| lactose sufficient for | 100 g |

This powder is diluted at the time of use with twice its weight in water at 40° C. to give a dark mauve mixture with a pH equal to 9.6. The viscosity is 6.5 poises. This mixture is applied to light brown hair for 30 minutes, rinsed and a shampoo is applied to the hair. After rinsing, the hair has a mauve brown glint and is glossy.

Example L

A dye plaster is prepared according to the invention by mixing the following ingredients:

| | |
|---|---|
| powder of residues of ethanol extraction of pulverized hawthorn having a granulometry less than 110μ | 30 g |
| powder of residues of ethanol extraction of pulverized horse chestnut having a granulometry less than 120 μ | 10 g |
| Lawsone (2-hydroxy-1,4-naphthoquinone) | 0.2 g |
| Maclurin (2,3',4,4'pentahydroxybenzophenone) | 3 g |
| red pectin 3 G sold by Unipectine | 3 g |
| citric acid | 4 g |
| trioxymethylene in powder | 0.3 g |
| instant skim milk powder | 100 g |

This powder is dispersed with twice its weight in water at 40° C., it gives a dull brown, creamy mixture with pH 4.1 and whose viscosity is 20 poises.

After application for 30 minutes on light blond hair, rinsing and shampooing, the hair exhibits a beautiful golden glint. The hair is glossy.

Example M

An oil plaster is prepared according to the invention by mixing the following ingredients:

| | |
|---|---|
| powder of residues of water extraction of plum tree evernia having a granulometry less than 20μ | 60 g |
| sunflower oil | 40 g |

This plaster is applied for 20 minutes to dirty hair then washed with a shampoo. After rinsing, the hair is glossy and soft to touch.

Example N

A makeup removal lotion for greasy skin is prepared according to the invention by mixing the following ingredients:

| | |
|---|---|
| mixture of glycerol stearate and polyoxyethylenated stearate sold under the tradename "ARLACEL 165" by the Atlas company | 1 g |
| stearic acid ester polyoxyethylenated with 8 moles of ethylene oxide sold under the tradename of "MYRJ 45" by the Atlas company | 3 g |
| mineral oil | 10 g |
| carboxyvinyl polymer with a high molecular weight sold under the tradename "CARBOPOL 940" by the Goodrich company | 10 g |
| powder of residues of ethanol extraction of micronized saponaria having a granulometry less than 20μ | 5 g |
| 20% triethanolamine in water | 1 g |
| preservative | 0.3 g |
| perfume | 0.4 g |
| water sufficient for | 100 g |

Example O

A care cream in the form of a water-in-oil emulsion is prepared according to the invention by mixing the following ingredients:

| | |
|---|---|
| mixture of aliphatic alcohols and waxes combined with oils and saturated hydrocarbons sold under the tradename "PROTEGIN X" by the Goldschmidt company | 20 g |
| mineral oil | 10 g |
| glycerin | 5 g |
| magnesium sulfate | 0.5 g |
| powder of residues of ethanol extraction of micronized saponaria having a granulometry less than 15μ | 10 g |
| preservative | 0.3 g |
| perfume | 0.4 g |
| water sufficient for | 100 g |

Example P

A cream for greasy skin in the form of oil-in-water emulsion is prepared according to the invention by mixing the following ingredients:

| | |
|---|---|
| stearic acid ester polyoxyethylenated with 8 moles of ethylene oxide sold under the tradename "MYRJ 45" by the Atlas company | 3.85 g |
| glycerol mono and di-stearate | 0.7 g |
| cetyl alcohol | 2.45 g |
| cyclic dimethyl polysiloxane sold under the tradename "VOLATIL SILICONE 7158" by the Union Carbide company | 5 g |
| sweet almond oil | 5 g |
| mixture of cetostearyl alcohol and sodium alkyl sufate sold under the tradename "SINNOWAX SX" by the Henkel company | 5 g |
| powder of residues of ethanol extraction of horse chestnut having a granulometry less than 20μ | 2 g |
| carboxyvinyl polymer "Carbopol 941" | 0.2 g |
| preservative | 0.3 g |
| perfume | 0.4 g |
| water sufficient for | 100 g |

Example Q

A body gel is prepared according to the invention by mixing the following ingredients:

| | |
|---|---|
| 96% ethyl alcohol | 15 g |
| carboxyvinyl polymer "CARBOPOL 940" | 30 g |
| powder of residues of ethanol extraction of horse chestnut having a granulometry less than 80μ | 5 g |
| 20% triethanolamine in water | 3 g |
| preservative | 0.2 g |
| perfume | 0.4 g |
| water sufficient for | 100 g |

Example R

A dry skin cream in the form of an oil-in-water emulsion is prepared according to the invention by mixing the following ingredients:

| | |
|---|---|
| glycerol monostearate associated with a polyoxyethylenated emulsifer sold under the name "SIMULSOL 165" by Seppic company | 6 g |
| sorbitan monostearate polyoxyethylenated with 20 moles of ethylene oxide (TWEEN 60) | 2 g |
| stearic acid | 2 g |
| cetyl alcohol | 1.2 g |
| liquid lanolin | 6 g |

| | |
|---|---|
| purcellin oil | 6 g |
| perhydrosqualene | 30 g |
| methylphenylpolysiloxane | 1 g |
| triethanolamine | 0.1 g |
| powder of residues of ethanol extraction of horse chestnut having a granulometry less than 10μ | 8 g |
| preservative | 0.3 g |
| perfume | 0.4 g |
| water sufficient for | 100 g |

Example S

A nail polish is prepared according to the invention by mixing the following ingredients:

| | |
|---|---|
| nitrocellulose | 18.8 g |
| Santolite MHP | 2 g |
| camphor | 1 g |
| dimethyl phthalate | 5 g |
| modified bentonite | 1.2 g |
| toluene | 8 g |
| charges and dye pigments | 2 g |
| powder of residues of ethanol extraction of saponsria having granulometry less than 20μ | 0.5 g |
| ethyl and butyl acetate | 100 g |

In this example the powder of the extraction residues is introduced as an opacifying agent.

We claim:

1. In a cosmetic composition for application to human hair or skin, said cosmetic composition containing a thickening or opacifying agent, the improvement comprising, as said thickening or opacifying agent, the residue of a plant extracted to remove all of its dye principles, said residue being in powder form having a granulometry less than 125 microns and being present in an amount ranging from 2 to 95 percent by weight based on the total weight of said composition.

2. In a cosmetic composition for application to human hair or skin, said cosmetic composition containing a thickening or opacifying agent, the improvement comprising, as said thickening or opacifying agent, the residue of a plant extracted to remove all of its essential oil principles, said residue being in powder form having a granulometry less than 125 microns and being present in an amount ranging from 2 to 95 percent by weight based on the total weight of said composition.

3. In a cosmetic composition for application to human hair or skin, said cosmetic composition containing a thickening or opacifying agent, the improvement comprising, as said thickening or opacifying agent, the residue of a plant extracted to remove all of its therapeutic or cosmetic active principles, said residue being in powder form having a granulometry less than 125 microns and being present in an amount ranging from 2 to 95 percent by weight based on the total weight of said composition.

4. In a cosmetic composition for application to human hair or skin, said cosmetic composition containing a thickening or opacifying agent, the improvement comprising, as said thickening or opacifying agent, the residue of a plant extracted to remove all of its olfactory principles, said residue being in powder form having a granulometry less than 125 microns and being present in an amount ranging from 2 to 95 percent by weight based on the total weight of said composition.

5. In a cosmetic composition for application to human hair or skin, said cosmetic composition containing a thickening or opacifying agent, the improvement comprising, as said thickening or opacifying agent, the residue of a plant extracted to remove all of its therapeutic or cosmetic active principles, said plant being selected from the group consisting of saponaria, ivy, eucalyptus, hawthorn, horsetail, arnica, ruscus, horse chestnut, and witch hazel and being extracted with ethanol, isopropanol, ethylene glycol or a mixture of water and ethylene glycol monoethyl ether, said residue being in powder form having a granulometry less than 125 microns and being present in an amount ranging from 2 to 95 percent by weight based on the total weight of said composition.

6. In a cosmetic composition for application to human hair or skin, said cosmetic composition containing a thickening or opacifying agent, the improvement comprising, as said thickening or opacifying agent, the residue of a plant extracted to remove all of its dye principles, said plant being nettle extracted with acetone, said residue being in powder form having a granulometry less than 125 microns and being present in an amount ranging from 2 to 95 percent by weight based on the total weight of said composition.

7. In a cosmetic composition for application to human hair or skin, said cosmetic composition containing a thickening or opacifying agent, the improvement comprising, as said thickening or opacifying agent, the residue of a plant extracted to remove all of its essential oil principles, said plant being selected from the group consisting of lavender, milfoil and rose and being extracted with a mixture of butane and isobutane, a mixture of water and ethanol, or hexane, said residue being in powder form having a granulometry less than 125 microns and being present in an amount ranging from 2 to 95 percent by weight based on the total weight of said composition.

8. In a cosmetic composition for application to human hair or skin, said cosmetic composition containing a thickening or opacifying agent, the improvement comprising, as said thickening or opacifying agent, the residue of a plant extracted to remove all of its olfactory principles, said plant being plum tree evernia extracted with water, said residue being in powder form having a granulometry less than 125 microns and being present in an amount ranging from 2 to 95 percent by weight based on the total weight of said composition.

9. A shampoo composition comprising an effective amount of an anionic, nonionic, cationic or amphoteric detergent and between 2 and 95 percent by weight of said composition of a plant extraction residue, as a thickening or opacifying agent for said composition, said residue being the remainder of the extraction of essentially all the active principles present in said plant, said plant being selected from the group consisting of saponaria, ivy, eucalyptus, and nettle and being extracted with a solvent selected from the group consisting of ethanol, isopropanol and acetone, said plant extraction residue being in powder form having a granulometry less than 125 microns.

10. A shampoo composition comprising an effective amount of an anionic, nonionic, cationic or amphoteric detergent and between 2 and 95 percent by weight of said composition of a plant extraction residue, as a thickening or opacifying agent for said composition, said residue being the remainder of the extraction of saponaria with ethanol and said residue having a granulometry less than 10μ.

11. A shampoo composition comprising an effective amount of an anionic, nonionic, cationic or amphoteric detergent and between 2 and 95 percent by weight of said composition of a plant extraction residue, as a thickening or opacifying agent for said composition, said residue being the remainder of the extraction of ivy with ethanol and said residue having a granulometry less than $10\mu$.

12. A shampoo composition comprising an effective amount of an anionic, nonionic, cationic or amphoteric detergent and between 2 and 95 percent by weight of said composition of a plant extraction residue, as a thickening or opacifying agent for said composition, said residue being the remainder of the extraction of nettle with acetone and said residue having a granulometry less than $10\mu$.

13. A shampoo composition comprising an effective amount of an anionic, nonionic, cationic or amphoteric detergent and between 2 and 95 percent by weight of said composition of a plant extraction residue, as a thickening or opacifying agent for said composition, said residue being the remainder of the extraction of eucalyptus with isopropanol and said residue having a granulometry less than $10\mu$.

* * * * *